United States Patent [19]

Gindler

[11] 4,207,203

[45] Jun. 10, 1980

[54] URIC ACID STANDARD SOLUTIONS

[75] Inventor: E. Melvin Gindler, Rockford, Ill.

[73] Assignee: Sherwood Medical Industries Inc., St. Louis, Mo.

[21] Appl. No.: 36,240

[22] Filed: May 4, 1979

Related U.S. Application Data

[63] Continuation of Ser. No. 896,731, Apr. 17, 1970, abandoned.

[51] Int. Cl.$^2$ .................. G01N 31/06; G01N 31/14; C09K 15/18; C09K 3/00
[52] U.S. Cl. .................. 252/408; 23/230 B; 424/3; 424/7; 435/10
[58] Field of Search .................. 252/408; 23/230 B; 195/103.5 R; 424/3, 7

[56] References Cited

U.S. PATENT DOCUMENTS

| | | | |
|---|---|---|---|
| 3,528,777 | 9/1970 | Moran | 252/408 |
| 3,822,115 | 7/1974 | Morin et al. | 252/408 |
| 3,920,400 | 11/1975 | Scheibe et al. | 252/408 |
| 4,072,627 | 2/1978 | Gindler | 252/408 |

OTHER PUBLICATIONS

Gindler, E., Clin. Chem., vol. 16, No. 6, p. 536 (1970).
Henry, R. J., *Clinical Chemistry Principles and Techniques,* Harper & Row, N.Y., pp. 964–965 (1974).

*Primary Examiner*—Teddy S. Gron
*Attorney, Agent, or Firm*—Stanley N. Garber; William R. O'Meara

[57] ABSTRACT

Stable aqueous solutions useful as standards in the determination of uric acid are disclosed. The solutions have a pH of about 6–7 and contain a buffer and a known concentration of uric acid present in solution as a salt of the pH-controlling buffer component. They do not contain any strong base such as lithium carbonate. The standards can be used in connection with either enzymatic or non-enzymatic procedures.

8 Claims, No Drawings

URIC ACID STANDARD SOLUTIONS

This is a continuation of application Ser. No. 896,731, filed Apr. 17, 1978, now abandoned.

The present invention relates to the determination of uric acid in biological fluids and, more particularly, to an improved uric acid standard solution which can be used in such determinations.

In man urate is the final product of the metabolism of purines, especially adenine and quanine which are constituents of all nucleic acids. In most other mammals, urate is further broken down by the enzyme, uricase, to allantoin, which is highly soluble. But, since man does not possess uricase, urate is not broken down further in the human body and this leads to the possibility of hyperuricemia which is an elevated serum uric acid concentration. Among other problems, hyperuricemia may give rise to the clinical syndrome of gout.

Clinical diagnostic determinations of uric acid in biological samples such as serum rely on the fact that uric acid can be oxidized to allantoin. Either the enzyme, uricase, or a non-enzymatic oxidant can be used. One non-enzymatic procedure uses, as the oxidizing agent, copper(II), in the presence of a color forming reagent such as 2,2'-bicinchoninate. See Gindler U.S. Pat. No. 4,072,627. Through oxidation, uric acid reduces copper(II) to copper(I) which, in turn, forms a colored complex with the bicinchoninate. The intensity of the complex, measured at 562 nm, correlates with the amount of copper(I) formed during oxidation of uric acid, and thus the concentration of uric acid present in the sample. Other procedures using non-enzymatic oxidants are shown in Moran U.S. Pat. No. 3,528,777 (phosphotungstate) and Morin, et. al. U.S. Pat. No. 3,822,115 (ferric ions).

To quantitatively determine the concentration of uric acid in the sample, it is customary to use the copper(II)-bicinchoninate system with standard solutions containing known concentrations of uric acid. Calibration graphs can then be constructed from standards containing different concentrations of uric acid for comparison with data obtained from samples containing the unknown concentrations.

Standard solutions containing uric acid in known concentrations have been available for a number of years. Gindler has observed that "A solution of uric acid in aqueous tris (hydroxymethyl) aminomethane is a rapidly prepared standard." Clin. Chem. 16, 536 (1970). Moreover, since uric acid itself is usually thought to be soluble in water only at a high pH, the solutions are ordinarily made under basic conditions with the use, for example, of a strong base such as lithium carbonate. See Clinical Diagnosis by Laboratory Methods, Clinical Chemistry, Todd-Sanford, Edn. 13, pp 451–452. Solutions so prepared are stable for an extended period of time when refrigerated. The necessity for refrigeration is, of course, a drawback where the standard is not going to be immediately used such as when initially formulated by a manufacturer, and then shipped to a customer for ultimate use.

Stable standard solutions of uric acid can, however, exist under acidic conditions when the uric acid is present as the N-hydroxymethyl adduct. See above identified Moran patent. First, an aqueous solution of the acid is prepared using lithium carbonate with heating at about 60° C. Then the adduct is formed by reaction with formaldehyde followed by acidification with a strong acid such as sulfuric acid. The formaldehyde adduct does not precipitate in acid solution and, being acidic, the solution is stable without refrigeration. Also, as conventionally prepared, standard solutions of uric acid contain various preservatives to inhibit microbial growth and chelating agents to bind various metal ions which might otherwise adversely affect stability by causing oxidation of the uric acid adduct.

While standard solutions based on the formaldehyde adduct of uric acid are useful in diagnostic procedures relying upon oxidation with non-enzymatic oxidants, they are not applicable with respect to all analytical methods, and particularly enzymatic methods such as those using uricase as the uric acid oxidant. Formaldehyde inhibits uricase and, accordingly, standards prepared with formaldehyde are not useful with some enzymatic procedures.

Scheibe, et. al. U.S. Pat. No. 3,920,400 is directed to a uric acid standard solution which is said to be useful in both enzymatic and chemical processes. The solution is described as "comprising an aqueous buffered solution of uric acid in the form of a lithium salt thereof, with a pH value of between 6 and 8, and at least one complexing agent for the higher valence stage of polyvalent heavy metal ions and/or an alkali azide". The solution is stated to be "remarkably stable". To form the solution, uric acid is dissolved in the presence of lithium carbonate and the pH of the solution adjusted to the indicated range with a suitable buffer. A phosphate buffer is preferred. Other buffers mentioned are imidazole, triethanolamine and tris.

There are at least two apparent problems accompanying the preparation of standards using lithium carbonate even without thereafter forming the formaldehyde adduct. Schiebe, et al. identify one; namely, the inevitability that small amounts of catalytically active metal ions will get into solution. The other is that to achieve solution either long stirring times or heating is required. Heating in alkaline solution can cause hydrolysis of uric acid while extended stirring time can be economically unattractive.

Accordingly, a principal object of the present invention is to provide a standard solution of uric acid which can be easily prepared at room temperature and which can be used in connection with both enzymatic and non-enzymatic procedures for determination of uric acid. A further object is to provide such a standard solution which is stable for extended periods without refrigeration and which can be conveniently stored and/or shipped.

In one of its aspects, the present invention provides a stable solution, useful as a standard in the determination of uric acid, which consists essentially of water, a buffer sufficient to maintain the pH value of the solution at about 6–7, and a known concentration of uric acid present as a soluble salt of the pH-controlling buffer component, the component having a pK value of about 5–7.5. The standard solution can be used in connection with either enzymatic or non-enzymatic procedures for the determination of uric acid, it can be easily prepared, and it is stable at an ambient temperature for at least about six months.

As used herein, the term "consists essentially of" means that the specified substances must be present, but that other substances which do not prevent the advantages of the invention from being realized can also be present. Accordingly, metal ions such as lithium and bases with a pK above about 8 such as tris and lithium carbonate are excluded from the solutions of the present invention. However, other substances such as one or more microbial growth inhibitors and chelating agents to bind metal ion impurities can and, in most instances, are present.

To prepare solutions of the present invention, a known concentration of uric acid can be dissolved in water in the presence of a buffer. The buffer and the amount thereof are selected such that the pH value of the solution is about 6-7 and, preferably 6.5-7. Dissolution of uric acid occurs rapidly at room temperature with the formation, in solution, of a uric acid salt with the pH-controlling buffer component. It is believed that the salt so formed is monobasic, i.e., only one of the hydroxyl groups of the acid is ionized.

Useful buffers are those having a pH-controlling component with a pK value of about 5-7.5. As used herein, the pH-controlling buffer component is that component of the buffer system which has the greatest buffer capacity at the pH value of the solution. Buffering capacity is a function of both the buffer component concentration and the difference between the solution pH value and the pK value of the component. It reaches a maximum at pH=pK and, therefore, the use of buffers with a component having a pK of about 6-7.5 is preferred. Buffers containing weakly basic amines, such as imidazole, pyridine, and collidine, are useful. In addition, organo-phosphorus compounds, such as trimethyl phosphorus, and conjugated oxygen compounds, such as pyrilium, are also useful. So long as pH control as above specified can be achieved, the selection of the acidic component of the buffer is not particularly critical. Weak acids, such as benzoic acid, acetic acid, propionic acid and the like, can be conveniently employed.

The following formulation illustrates a useful standard solution of the present invention which is stable for an extended period at room temperature and can be used in either enzymatic or non-enzymatic procedures.

2.000 gm uric acid
13.6 gm imidazole (0.200 mole)
0.3 gm ethylene diamine tetraacetic acid (chelating agent)
26.88 gm phenoxyethanol (preservative)
12.2 gm benzoic acid (0.100 mole for pH control through buffer formation with imidazole and as preservative)
0.5 gm sodium azide (preservative)
500 ml isopropanol (preservative)
Sufficient deionized or distilled water to bring solution to 2.00 liters.

The above solution has a pH value of 6.85 and contains uric acid in a concentration of 100 mg/dl. Standard solutions with different concentrations can be prepared by appropriately diluting this solution.

While the present invention has been illustrated in connection with certain preferred embodiments, it is to be understood that the invention is not to be limited to those embodiments disclosed. On the contrary, it is intended that the invention cover all modifications and alternatives falling within the sphere and scope of the invention as expressed in the appended claims.

I claim:

1. A stable solution useful as a standard in the determination of uric acid, said solution consisting essentially of water, a buffer sufficient to maintain the pH value of the solution at about 6-7, and a known concentration of uric acid present as a soluble salt of the pH-controlling buffer component, said component having a pK value of about 5-7.5, and said solution having excluded therefrom bases with a pK above about 8.

2. The solution of claim 1 which also contains one or more microbial growth inhibitors and metal chelating agents.

3. The solution of claim 2 wherein the pH-controlling buffer component has a pK value of 6-7.5.

4. The solution of claim 3 wherein the buffer comprises a weakly basic amine.

5. The solution of claim 4 wherein the amine is imidazole, pyridine or collidine.

6. The solution of claim 5 wherein the pH value is 6.5-7.

7. The solution of claim 6 wherein the amine is imidazole.

8. The solution of claim 7 wherein the acidic component of the buffer is benzoic acid.

* * * * *